United States Patent
Booksh et al.

(10) Patent No.: US 7,281,857 B2
(45) Date of Patent: Oct. 16, 2007

(54) POLYMER CONNECTORS FOR USE IN SURFACE PLASMON RESONANCE SENSOR

(75) Inventors: Karl S. Booksh, Gilbert, AZ (US); Jean-Francois Masson, Decatur, GA (US)

(73) Assignee: Arizona Board of Regents, a body corporate acting for and on behalf of Arizona State University, Tempe, AZ (US)

( * ) Notice: Subject to any disclaimer, the term of this patent is extended or adjusted under 35 U.S.C. 154(b) by 142 days.

(21) Appl. No.: 10/558,021

(22) PCT Filed: May 28, 2004

(86) PCT No.: PCT/US2004/017069

§ 371 (c)(1), (2), (4) Date: Nov. 22, 2005

(87) PCT Pub. No.: WO2004/106892

PCT Pub. Date: Dec. 9, 2004

(65) Prior Publication Data

US 2007/0058905 A1 Mar. 15, 2007

Related U.S. Application Data

(60) Provisional application No. 60/473,861, filed on May 28, 2003.

(51) Int. Cl.
*G02B 6/38* (2006.01)
*G02B 6/36* (2006.01)

(52) U.S. Cl. .............................. 385/55; 385/53; 385/88

(58) Field of Classification Search .................. 385/53, 385/55, 59, 60, 71, 88, 147
See application file for complete search history.

(56) References Cited

U.S. PATENT DOCUMENTS

| | | | |
|---|---|---|---|
| 5,973,862 A | 10/1999 | Hashizume | 359/819 |
| 6,298,190 B2 | 10/2001 | Waldron et al. | 385/134 |
| 2001/0010747 A1* | 8/2001 | Dourdeville et al. | 385/147 |

* cited by examiner

*Primary Examiner*—Quyen P Leung
(74) *Attorney, Agent, or Firm*—McDonnell Boehnen Hulbert & Berghoff LLP

(57) ABSTRACT

A device for connecting optical components of a fiber optic probe and a jumper in a Surface Plasmon Resonator (SPR) has two high-pressure-liquid-chromatography (HPLC) polyetheretherketone (PEEK) connectors, one containing the optical fibers from a probe and the other containing optical fibers which link to a detector and a light source. A method of joining a probe's distal end to a jumper, with at least two fibers or a multimode fiber connected to a light source and to a detection apparatus, has the steps of covering the distal end of the probe with a plastic sleeve, placing the sleeved distal end into a PEEK connector, trimming the distal end of the probe to be even with the edge of the PEEK connection, and connecting the PEEK connector with the jumper.

17 Claims, 2 Drawing Sheets

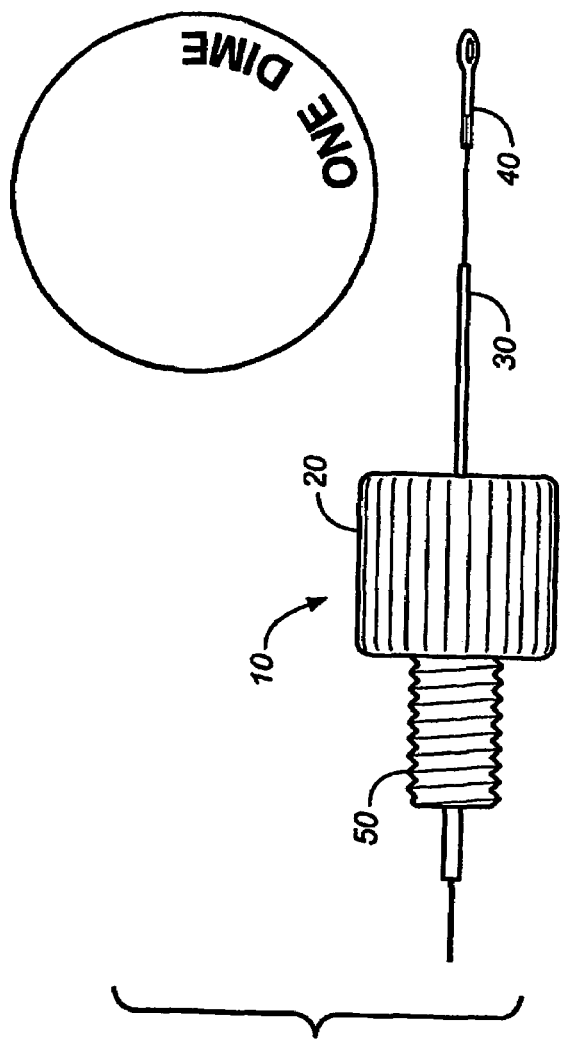
FIG._1
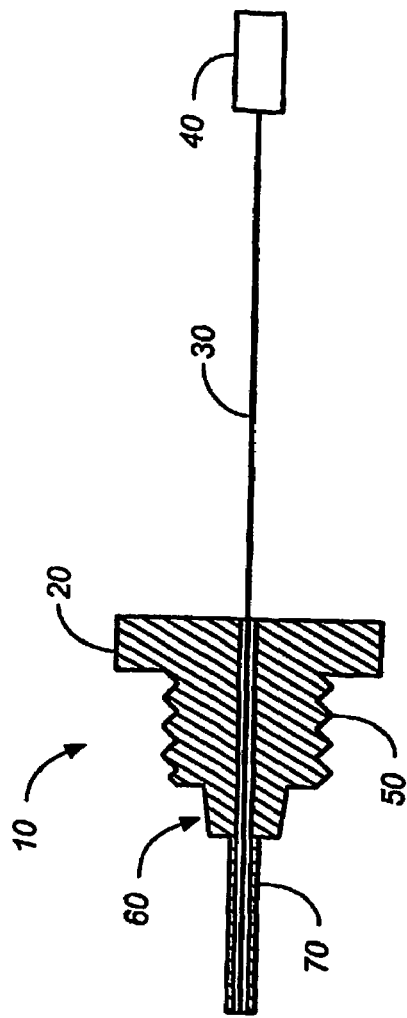
FIG._2

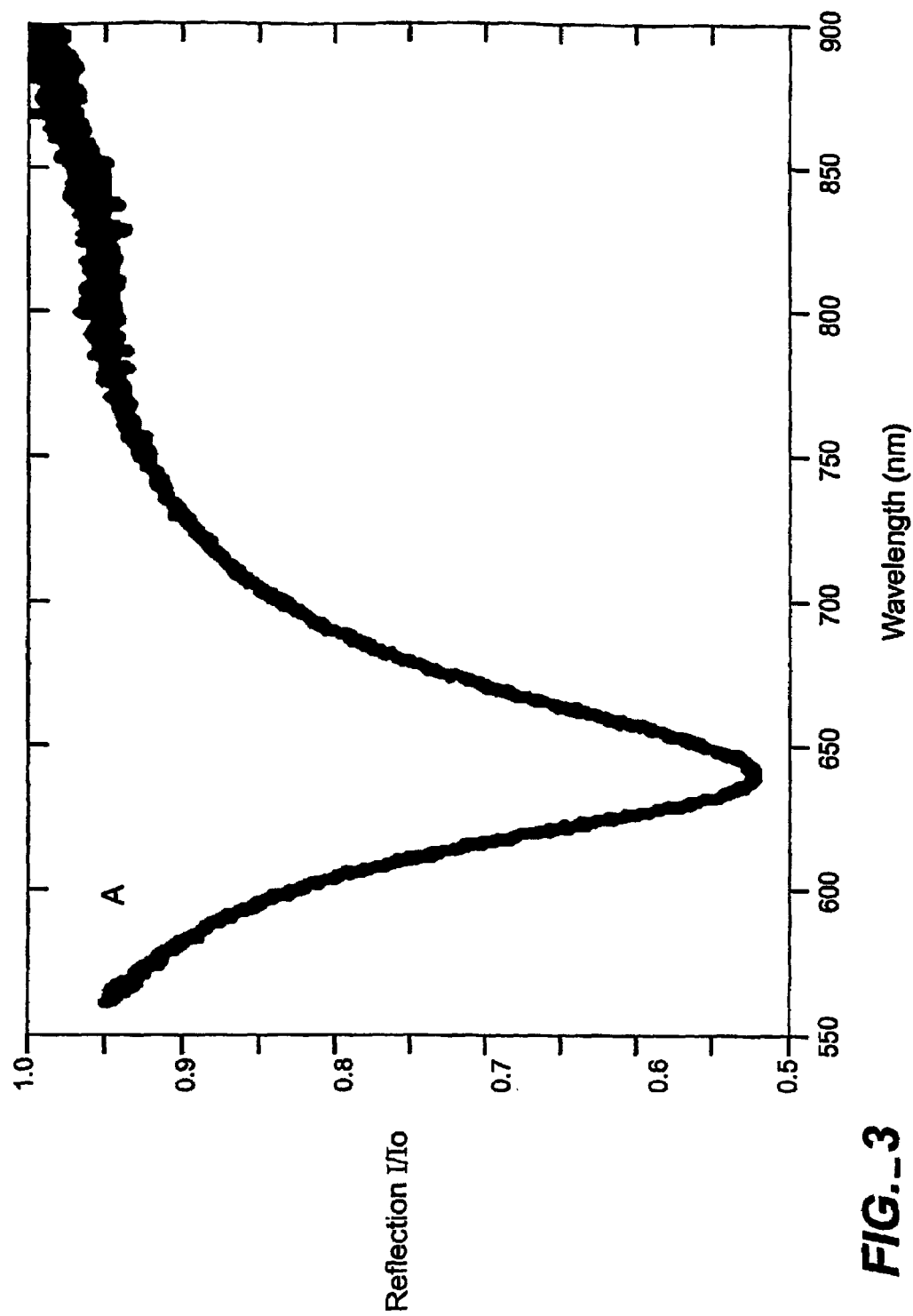
FIG._3

POLYMER CONNECTORS FOR USE IN SURFACE PLASMON RESONANCE SENSOR

CLAIM TO DOMESTIC PRIORITY

This application is a U.S. National Stage Application filed under 35 U.S.C. 371 claiming priority from the International Application No. PCT/US2004/0 17069, filed May 28, 2004, which claims the benefit of United States Provisional Patent Application Ser. No. 60/473,861, filed May 28, 2003, and which applications are incorporated herein by reference.

BACKGROUND

1. Technical Field

This invention concerns Surface Plasmon Resonance (SPR) spectroscopy and more specifically, a reusable coupling device for connecting the optical fiber and jumper in a SPR probe.

2. Prior Art

In wide use in the SPR field are SMA connectors. SMA is an acronym for SubMiniature version A and was developed in the 1960's. SMA connectors are widely used in the electronics and cable communication industries. A typical SMA connector for small-gauge fiber-optics weighs about 6 grams, costs approximately 9 dollars US and can be used about two to three times.

What is needed is a lighter weight, less costly and more reusable fiber-optic connector.

SUMMARY OF THE INVENTION

In one embodiment, there is disclosed a device for connecting optical components of a fiber optic probe and a jumper in a Surface Plasmon Resonator (SPR) comprising two high-pressure-liquid-chromatography (HPLC) polyetheretherketone (PEEK) connectors, one containing the optical fibers from a probe and the other containing optical fibers which link to a detector and a light source. In this device the connectors may be joined by an HPLC union that affords a zero-volume junction.

In another embodiment, there is disclosed a method of joining an SPR probe's distal end to a jumper with at least two fibers or a multimode fiber connected to a light source and to a detection apparatus. The method includes the steps of covering the distal end of the probe with a plastic sleeve, placing the sleeved distal end into a PEEK connector, trimming the distal end of the probe to be even with the edge of the PEEK connection; and connecting the polyetheretherketone (PEEK) connector with the jumper. In another embodiment, the jumper and the PEEK connector can be joined with an HPLC PEEK union.

BRIEF DESCRIPTION OF THE DRAWING FIGURES

FIG. 1 illustrates the size of a SPR probe and the connector of the present invention, illustrating the size of the probe relative to the size of a United States dime.

FIG. 2 shows a cross-section of the inventive connector, into which the fiber optic shielded probe and a jumper have been inserted.

FIG. 3 shows the spectra obtained with the new SPR utilizing the HPLC PEEK connector.

DETAILED DESCRIPTION OF A PREFERRED EMBODIMENT

A new fiber optic connector has been designed to provide lighter weight, more reuses (greater than about 10), and roughly half the cost of the currently available SMA connectors. It uses a threaded interface.

The connector, incorporating HPLC fluidic technology, may be used in place of expensive SMA connectors currently used for optical applications. In the connector, an optical fiber is fixed into a capillary sleeve and mounted in one port of the HPLC PEEK connector. The other port is used for a fiber optic jumper. The optical coupling between the optical fiber and the fiber(s) in the jumper results in a zero volume union. The connector is useful in SPR because of its low cost, ease of reuse, excellent coupling quality, low weight and ease of deposition of the gold layer in SPR applications.

FIG. 1 shows the SPR probe 10 with the PEEK connector 20. Into the connector, the probe 30 with a sensing area 40 has been inserted. The PEEK connector shown has a threaded end 50, which in some embodiments can be threaded into a HPLC union. The SPR probe is pictured with a United States dime, for size comparison.

FIG. 2 shows a cross-section of the SPR probe 10 with the PEEK connector 20. The optical fiber 30, in addition to the sensing area 40, has a sleeve 70, which has been glued in place by epoxy. The optical fiber 30 in the sleeve 60 passes through the connector 20 to a ferrule 60. The end of the optical fiber 30 extending beyond the ferrule 60 is trimmed to be flush with the polishing disk.

A jumper (not shown) was made with the same type of PEEK connector. The jumper had two 200 μm fibers, one connected with the optical fiber 30 in the PEEK connector 20. One fiber of the jumper connected with a light source and the other end connected to a detector. An HPLC union was used to connect the probe to the jumper. In this embodiment, a zero-volume union was used.

The whole combination was tested in ethanol and air. FIG. 3 shows the spectrum taken when the exposure time was 300 milliseconds and the delay was 500 milliseconds. The intensity of light at the detector seemed higher than with previous connectors. The spectrum exhibited a sharp decrease in intensity characteristic of the SPR signal for ethanol when referenced to air.

Table 1 summarizes a comparison between a prior art SMA connector and the inventive PEEK SMA connector.

TABLE 1

|  | SMA | PEEK |
| --- | --- | --- |
| Weight (g) | 6.15 | 0.65 |
| Cost (US$ in 2002) | 8.75 | 4.13 |
| Number of Reuses | 2-3 | >10 |

Preparation of SPR Probe and Connector

The optical fibers used for SPR probes are approximately 400 μm in diameter, although sizes as small as 50 μm can be used. Before connection, the optical fiber was inserted into a plastic sleeve, made of PEEK. The dimensions of the capillary sleeve are approximately 1.59 mm external diameter and 395 μm internal diameter. The optical fiber is fixed inside the capillary sleeve with glue, preferably epoxy. Then the HPLC PEEK connector is mounted with a ferrule on the capillary sleeve with the optical fiber. To gauge the length of the probe, it is mounted on a custom-made chuck that also serves as a polishing disk. The chuck provides a zero-volume union cut exactly in the middle and mounted on a stainless steel disk. Then the SPR probe is prepared by depositing gold on the fiber optic using a sputter coater. The optical fiber end is evenly coated using a rotation stage. The finished product is shown in FIG. 1.

Coupling of Probe to a Fiber Optic Jumper

To couple the probe to a fiber optic jumper, a jumper containing two fibers, one for light emission and the second for light collection is used. The jumper is made from 200 μm core fiber optics and is mounted in a sleeve of approximately 1.59 mm external diameter and 455 μm internal diameter. The coupling between the probe and the jumper was achieved with a zero-volume union. SPR signals were obtained proving that the new type of connector works effectively.

Although the invention has been described in detail with reference to the presently preferred embodiments, those of ordinary skill in the art will appreciate that various modifications can be made without departing from the invention. Accordingly, the invention is defined only by the following claims.

What is claimed is:

1. A device for connecting components of a fiber optic probe and a jumper in a Surface Plasmon Resonator (SPR) comprising:
   a first high-pressure-liquid-chromatography (HPLC) polyetheretherketone (PEEK) connector enclosing a portion of a first optical fiber; and
   a second HPLC PEEK connector enclosing a portion of a second optical fiber optically coupled to the first optical fiber, wherein the first and second HPLC PEEK connectors are joined by a zero-volume junction.

2. The device of claim 1, wherein the second optical fiber is used for the jumper.

3. The device of claim 1, wherein the second optical fiber receives a detector and a light source.

4. The device of claim 1, wherein the first optical fiber is fixed into a capillary sleeve.

5. The device of claim 4, wherein the capillary sleeve is mounted to a first port of the first HPLC PEEK connector.

6. A method of joining a fiber optic probe to a jumper with at least two fibers or a multimode fiber connected to a light source and to a detection apparatus, the method comprising:
   covering a distal end of the fiber optic probe with a sleeve;
   placing the sleeved distal end into a polyetheretherketone (PEEK) connector;
   trimming the distal end of the fiber optic probe to be even with the edge of the PEEK connector; and
   connecting the PEEK connector with the jumper.

7. The method of claim 6, further including connecting the PEEK connector with the jumper using an HPLC PEEK union.

8. The method of claim 7, wherein the HPLC PEEK union is configured as a zero-volume junction.

9. The method of claim 6, wherein covering a distal end of the fiber optic probe with a plastic sleeve further includes securing an optical fiber inside the sleeve using an epoxy.

10. The method of claim 6, further including depositing a gold coating on a portion of the fiber optic probe using a sputter coater.

11. The method of claim 10, wherein the portion of the fiber optic probe is evenly coated using a rotation stage.

12. The method of claim 6, wherein trimming the distal end of the fiber optic probe to be even with the edge of the PEEK connection is performed using a polishing disk.

13. A method of manufacturing a device for connecting optical components of a fiber optic probe and a jumper in a Surface Plasmon Resonator (SPR) comprising:
   providing a first high-pressure-liquid-chromatography (HPLC) polyetheretherketone (PEEK) connector having a first optical fiber;
   providing a second HPLC PEEK connector having a second optical fiber optically coupled to the first optical fiber; and
   joining the first and second HPLC PEEK connectors by a zero-volume junction.

14. The method of claim 13, wherein the second optical fiber is used for a fiber optic jumper.

15. The method of claim 13, wherein the second optical fiber receives a detector and a light source.

16. The method of claim 13, wherein the first optical fiber is fixed into a capillary sleeve.

17. The device of claim 16, wherein the capillary sleeve is mounted to a first port of the first HPLC PEEK connector.

* * * * *